US012234210B2

(12) United States Patent
Patterson et al.

(10) Patent No.: US 12,234,210 B2
(45) Date of Patent: *Feb. 25, 2025

(54) SYNTHESIS OF NIROGACESTAT

(71) Applicant: SpringWorks Therapeutics, Inc., Stamford, CT (US)

(72) Inventors: Kristin Patterson, Stamford, CT (US); Mark Hatcher, Stamford, CT (US)

(73) Assignee: SPRINGWORKS THERAPEUTICS, INC., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/304,202

(22) Filed: Apr. 20, 2023

(65) Prior Publication Data
US 2023/0312480 A1  Oct. 5, 2023

Related U.S. Application Data

(63) Continuation of application No. PCT/US2022/075839, filed on Sep. 1, 2022.

(60) Provisional application No. 63/239,696, filed on Sep. 1, 2021.

(51) Int. Cl.
C07D 233/88 (2006.01)
C07C 227/26 (2006.01)
C07D 263/44 (2006.01)

(52) U.S. Cl.
CPC .......... C07D 233/88 (2013.01); C07C 227/26 (2013.01); C07D 263/44 (2013.01)

(58) Field of Classification Search
CPC .................................................. C07D 233/88
See application file for complete search history.

(56) References Cited

U.S. PATENT DOCUMENTS

| | | | |
|---|---|---|---|
| 7,342,118 B2 | 3/2008 | Brodney et al. | |
| 7,795,447 B2 | 9/2010 | Brodney et al. | |
| 7,951,958 B2 | 5/2011 | Brodney et al. | |
| 10,590,087 B1 | 3/2020 | Greer et al. | |
| 10,710,966 B1 | 7/2020 | Greer et al. | |
| 10,941,118 B2 | 3/2021 | Greer et al. | |
| 11,504,354 B1 * | 11/2022 | Patterson | A61K 45/06 |
| 11,612,588 B1 * | 3/2023 | Patterson | A61K 9/20 514/400 |
| 11,807,611 B2 * | 11/2023 | Patterson | A61K 31/417 |
| 11,844,780 B2 * | 12/2023 | Patterson | A61K 9/20 |
| 2005/0107381 A1 | 5/2005 | Chen | |
| 2005/0215610 A1 * | 9/2005 | Brodney | A61P 9/12 514/397 |
| 2005/0222219 A1 | 10/2005 | Chen | |
| 2010/0184737 A1 | 7/2010 | Brodney | |
| 2016/0354382 A1 | 12/2016 | Pajvani | |
| 2018/0194773 A1 | 7/2018 | Ban et al. | |
| 2018/0214553 A1 | 8/2018 | Berenson | |
| 2019/0161553 A1 | 5/2019 | Sather et al. | |
| 2019/0359727 A1 | 11/2019 | Riddell et al. | |
| 2019/0367628 A1 | 12/2019 | Abujoub et al. | |
| 2020/0055948 A1 | 2/2020 | Daley et al. | |
| 2020/0179511 A1 | 6/2020 | Daley et al. | |
| 2021/0040045 A1 | 2/2021 | Greer et al. | |
| 2021/0269407 A1 | 9/2021 | Greer et al. | |
| 2023/0049311 A1 | 2/2023 | Cheng et al. | |
| 2023/0087828 A1 | 3/2023 | Cheng et al. | |
| 2023/0088856 A1 | 3/2023 | Patterson et al. | |
| 2023/0089434 A1 | 3/2023 | Patterson et al. | |
| 2023/0090557 A1 | 3/2023 | Patterson et al. | |
| 2023/0091097 A1 | 3/2023 | Patterson et al. | |
| 2023/0091415 A1 | 3/2023 | Patterson et al. | |
| 2023/0112444 A1 | 4/2023 | Balakumaran et al. | |
| 2023/0121547 A1 | 4/2023 | Shearer et al. | |

FOREIGN PATENT DOCUMENTS

| | | | |
|---|---|---|---|
| WO | WO-0049037 A1 | 8/2000 | |
| WO | WO-0210141 A1 | 2/2002 | |
| WO | WO-2005092864 A1 | 10/2005 | |
| WO | WO-2013153391 A1 | 10/2013 | |
| WO | WO-2016120216 A1 | 8/2016 | |
| WO | WO-2016166630 A1 | 10/2016 | |
| WO | WO-2018045273 A2 | 3/2018 | |
| WO | WO-2018151836 A1 | 8/2018 | |
| WO | WO-2018201051 A1 | 11/2018 | |
| WO | WO-2018201056 A1 | 11/2018 | |
| WO | WO-2019053727 A1 | 3/2019 | |
| WO | WO-2019090364 A1 | 5/2019 | |
| WO | WO-2020092848 A2 | 5/2020 | |
| WO | WO-2020092854 A2 | 5/2020 | |
| WO | WO-2020208572 A1 * | 10/2020 | ........... A61K 31/417 |
| WO | WO-2021029854 A1 | 2/2021 | |
| WO | WO-2021146604 A1 | 7/2021 | |
| WO | WO-2021183934 A1 | 9/2021 | |
| WO | WO-2023039475 A1 | 3/2023 | |

OTHER PUBLICATIONS

Brodney, et al. Bioorganic & Medicinal Chemistry Letters 21 (2011) 2637-2640.*
Brodney, et al. Design, synthesis, and in vivo characterization of a novel series of tetralin amino imidazoles as γ-secretase inhibitors: Discovery of PF-3084014, (Bioorganic & Medicinal Chemistry Letters 21, 2637-2640). (Year: 2011).*
Robinson, Control of Genotoxic Impurities in Active Pharmaceutical Ingredients: A review and Perspective (Organic Process Research & Development, 14, 946-959). (Year: 2010).*
Jadhav et al. A Comprehensive Review for the Learners and Users: Preparative High Performance Liquid Chromatography, (IJCPA, 1(3), 121-129). (Year: 2014).*

(Continued)

Primary Examiner — Matthew P Coughlin
Assistant Examiner — Meghan C Heasley
(74) Attorney, Agent, or Firm — Blank Rome LLP

(57) ABSTRACT

The present disclosures are directed to processes for synthesizing (S)-2-(((S)-6,8-difluoro-1,2,3,4-tetrahydronaphthalen-2-yl)amino)-N-(1-(2-methyl-1-(neopentylamino)propan-2-yl)-1H-imidazol-4-yl)pentanamide ("nirogacestat").

4 Claims, No Drawings

(56) References Cited

OTHER PUBLICATIONS

Aurora Building Blocks, Chemical Abstracts Service, Accession No. 1962925-29-6, accessed through STN database on Feb. 21, 2020, American Chemical Society, United States, 1 page (published Feb. 21, 2019).
Berge, S.M., et al., "Pharmaceutical Salts," Journal of Pharmaceutical Sciences 66(1):1-19, Elsevier, United States (Jan. 1977).
Bierer, B.E., et al., "Cyclosporin A and FK506: Molecular Mechanisms of Immunosuppression and Probes for Transplantation Biology," Current Opinion in Immunology 5(5):763-773, Elsevier, United Kingdom (Oct. 1993).
Bird, R.E., et al., "Single-chain Antigen-binding Proteins," Science 242(4877):423-426, Association for the Advancement of Science, United States (Oct. 1988).
Co-pending U.S. Appl. No. 17/995,031, inventors Patterson, K., et al., filed Sep. 8, 2022 (Not yet Published).
CAS Registry No. 1290543-63-3, Substance Detail, retrieved from SciFinder CAS, accessed on Aug. 29, 2022, 3 pages.
ClinicalTrials.gov, "A Study Evaluating PF-03084014 in Patients With Advanced Breast Cancer With or Without Notch Alterations," NCT02299635, accessed at https://clinicaltrials.gov/ct2/show/NCT02299635?term=03084014&rank=1, accessed on Nov. 7, 2022, 8 pages.
ClinicalTrials.gov, "A Study Of PF-03084014 In Japanese Patients With Advanced Solid Tumors," NCT02462707, accessed at https://clinicaltrials.gov/ct2/show/NCT02462707?term=NCT02462707&draw=2&rank=1, accessed on Nov. 8, 2022, 5 pages.
ClinicalTrials.gov, "A Study Evaluating the PF-03084014 in Combination With Docetaxel in Patients With Advanced Breast Cancer," NCT01876251, accessed at https://clinicaltrials.gov/ct2/show/NCT01876251?term=03084014&rank=6, accessed on Nov. 7, 2022, 10 pages.
ClinicalTrials.gov, "A Trial in Patients With Advanced Cancer and Leukemia," NCT00878189, accessed at https://clinicaltrials.gov/ct2/show/NCT00878189?term=03084014&rank=9, accessed on Nov. 8, 2022, 16 pages.
ClinicalTrials.gov, "Biomarker Research Study for PF-03084014 in Chemoresistant Triple-negative Breast Cancer (RHEA)," NCT02338531, accessed at https://clinicaltrials.gov/ct2/show/NCT02338531?term=03084014&rank=5, accessed on Nov. 8, 2022, 6 pages.
ClinicalTrials.gov, "Compassionate Use Protocol for PF-03084014 in Patients With Advanced Solid Tumor Malignancies," NCT02955446, accessed at https://clinicaltrials.gov/ct2/show/NCT02955446?term=03084014&rank=7, accessed on Nov. 8, 2022, 5 pages.
ClinicalTrials.gov, "Gamma Secretase Inhibitor PF-03084014 in Treating Patients With AIDS-Associated Kaposi Sarcoma," NCT02137564, accessed at https://clinicaltrials.gov/ct2/show/NCT02137564?term=03084014&rank=2, accessed on Nov. 8, 2022, 9 pages.
ClinicalTrials.gov "Nirogacestat for Adults with Desmoid Tumor/Aggressive Fibromatosis (DT/AF) (DeFi)," NCT03785964, accessed at https://clinicaltrials.gov/ct2/show/NCT03785964?term=nirogacestat&rank=1, accessed on Nov. 8, 2022, 10 pages.
ClinicalTrials.gov, "Phase II Trial of the Gamma-Secretase Inhibitor PF-03084014 in Adults With Desmoid Tumors/Aggressive Fibromatosis," NCT01981551, accessed at https://clinicaltrials.gov/ct2/show/NCT01981551?term=03084014&rank=4, accessed on Nov. 8, 2022, 11 pages.
ClinicalTrials.gov, "Study of PF-03084014 in Combination With Gemcitabine and Nab-Paclitaxel in Patients With Metastatic Pancreatic Adenocarcinoma Not Previously Treated With Anticancer Therapies," NCT02109445, accessed at https://clinicaltrials.gov/ct2/show/NCT02109445?term=03084014&rank=8, accessed on Nov. 8, 2022, 12 pages.
ClinicalTrials.gov, "Platform Study of Belantamab Mafodotin as Monotherapy and in Combination With Anti-cancer Treatments in Participants With Relapsed/Refractory Multiple Myeloma (RRMM) (Dreamm 5)," NCT04126200, accessed at https://clinicaltrials.gov/ct2/show/NCT04126200?term=NCT04126200draw=2rank=1, accessed on Nov. 8, 2022, 25 pages.
ClinicalTrials.gov, "PF-06863135 As Single Agent And In Combination With Immunomodulatory Agents In Relapse/Refractory Multiple Myeloma," NCT03269136, accessed at https://clinicaltrials.gov/ct2/show/NCT03269136?term=NCT03269136draw=2rank=1, accessed on Jul. 19, 2022, 10 pages.
ClinicalTrials.gov, "Safety and Efficacy of ALLO-715 BCMA Allogenic CAR T Cells in in Adults With Relapsed or Refractory Multiple Myeloma (Universal) (Universal)," NCT04093596, accessed at https://clinicaltrials.gov/ct2/show/NCT04093596?term=NCT04093596draw=2rank=1, accessed on Jul. 19, 2022, 10 pages.
Cowan, A., et al., "Efficacy and Safety of Fully Human Bema CAR T Cells in Combination with a Gamma Secretase Inhibitor to Increase Bema Surface Expression in Patients with Relapsed or Refractory Multiple Myeloma," Blood 134(S1):204, American Society of Hematology, United States (Nov. 2019).
Eastman, S., et al., "Synergistic Activity of Belantamab Mafodotin (anti-BCMA immune-conjugate) with PF-03084014 (gamma-secretase inhibitor) in Bema-Expressing Cancer Cell Lines," Blood 134(S1):4401, American Society of Hematology, United States (2019).
Henderson, D.J., et al., "Comparison of the Effects of FK-506, Cyclosporin A and Rapamycin on IL-2 Production," Immunology 73(3):316-321, Blackwell Scientific Publications, United Kingdom (Jul. 1991).
International Search Report and Written Opinion for International Application No. PCT/US2019/045948, European Patent Office, Netherlands, mailed Jul. 6, 2020, 9 pages.
International Search Report and Written Opinion for International Application No. PCT/US2021/013705, European Patent Office, Netherlands, mailed May 7, 2021, 11 pages.
International Search Report and Written Opinion for International Application No. PCT/US2021/022177, European Patent Office, Netherlands, mailed Jun. 24, 2021, 13 pages.
Kummar, S., et al., "Clinical Activity of the γ-Secretase Inhibitor PF-03084014 in Adults With Desmoid Tumors (Aggressive Fibromatosis)," J. Clin. Oncology 35(14):1561-9, American Society of Clinical Oncology, United States (2017).
Liu, J., et al., "Inhibition of T Cell Signaling by Immunophilin-ligand Complexes Correlates With Loss of Calcineurin Phosphatase Activity," Biochemistry 31(16):3896-3901, American Chemical Society, United States (Apr. 1992).
Millipore Sigma, "PF-03084014 hydrobromide," SigmaAldrich.com, accessed at https://www.sigmaaldrich.com/catalog/product/sigma/pz0298?lang=en®ion=US, accessed on Nov. 8, 2022, 4 pages.
Nazarian, A.A., et al., "Characterization of Bispecific T-cell Engager (BiTE) Antibodies With a High-capacity T-cell Dependent Cellular Cytotoxicity (TDCC) Assay," Journal of Biomolecular Screening 20(4):519-527, Sage Publications, United States (Apr. 2015).
Pont, M.J., et al., "γ-Secretase Inhibition Increases Efficacy of BCMA-specific Chimeric Antigen Receptor T Cells in Multiple Myeloma," Blood 134(19):1585-1597, Elsevier, United States (Nov. 2019).
*Remington's Pharmaceutical Sciences*, 18th edition, Gennaro, A.R., ed., pp. 172-174, Mack Publishing, Easton, Pennsylvania, United States, (1990).
Saif, M.A., et al., "In vivo T-cell Depletion Using Alemtuzumab in Family and Unrelated Donor Transplantation for Pediatric non-Malignant Disease Achieves Engraftment with Low Incidence of Graft vs. Host Disease," Pediatric Transplantation 19(2):211-218, Wiley, United States (Mar. 2015).
Shang, H., et al., "Targeting the Notch Pathway: A Potential Therapeutic Approach for Desmoid Tumors," Cancer 121(22):4088-96, Wiley-Liss, United States (2015).
Silverman, R.B., pp. 29-32 in *The Organic Chemistry of Drug Design and Drug Action*, Second Edition, Elsevier Academic Press, United States (2004).
Sommer, C., et al., "Preclinical Evaluation of Allogeneic CAR T Cells Targeting BCMA for the Treatment of Multiple Myeloma," Molecular Therapy 27(6):1126-1138, Cell Press, United States (Jun. 2019).

(56) References Cited

OTHER PUBLICATIONS

Takahashi, T., et al., "Safety and efficacy of gamma-secretase inhibitor nirogacestat (PF-03084014) in desmoid tumor: Report of four pediatric/young adult cases," Pediatr. Blood Cancer 67(10):e28636, Wiley, United States (Jul. 2020).

The United States Pharmacopeia—National Formulary, "941 X-ray Diffraction," 23rd Edition, NF-18, pp. 1843-1844, The United States Pharmacopeial Convention, United States (1995).

UniProtKB, "TNR17_HUMAN," Accession No. Q02223, UniProt. org, accessed at https://www.uniprot.org/uniprotkb/Q02223/entry, on Nov. 7, 2022, 6 pages.

Wei, P., et al., "Evaluation of Selective γ-Secretase Inhibitor PF-03084014 for Its Antitumor Efficacy and Gastrointestinal Safety to Guide Optimal Clinical Trial Design," Molecular Cancer Therapeutics 9(6):1618-28, American Association for Cancer Research, United States (2010).

Pub Chem AKOS03764977, 2005.

International Search and Written Opinion issued in PCT/US2022/075839 on Jan. 27, 2023.

PubChem-SID-340503698, Modify Date: Nov. 20, 2020 (Nov. 20, 2020), p. 2, figure, this is a purchasable chemical.

PubChem-SID-441886460, Modify Date: Jul. 20, 2021 (Jul. 20, 2021), p. 2, figure, this is a purchasable chemical.

\* cited by examiner

SYNTHESIS OF NIROGACESTAT

FIELD OF THE DISCLOSURE

The present disclosure relates to processes of synthesizing (S)-2-(((S)-6,8-difluoro-1,2,3,4-tetrahydronaphthalen-2-yl)amino)-N-(1-(2-methyl-1-(neopentylamino)propan-2-yl)-1H-imidazol-4-yl)pentanamide ("nirogacestat" or "Compound 1").

BACKGROUND (S)-2-(((S)-6,8-difluoro-1,2,3,4-tetrahydronaphthalen-2-yl)amino)-N-(1-(2-methyl-1-(neopentylamino)propan-2-yl)-1H-imidazol-4-yl)pentanamide ("nirogacestat" or "Compound 1") exhibits promising activity for the treatment of tumors or cancer, such as desmoid tumors, multiple myeloma, a cancer having a mutation in a Notch pathway gene, adenoid cystic carcinoma, and T-cell acute lymphoblastic leukemia (U.S. Pat. No. 10,590,087). A known route of synthesizing nirogacestat offers few points for the control of impurities other than at the final isolation (*Bioorganic & Medicinal Chemistry Letters* 21:2637-2640 (2011)). If control of impurities is not optimal in the late stage intermediates, impurities are likely to be present in the product at reportable levels. This route also exhibits a low yield when a norvaline moiety and tetralone fragments are coupled (*Bioorganic & Medicinal Chemistry Letters* 21:2637-2640 (2011)). Therefore, there exists a need for developing a new route to introduce additional control points to purge impurities and minimize any loss of stereochemical integrity.

BRIEF SUMMARY OF THE DISCLOSURE

Processes comprising reacting a novaline moiety with 1,1'-carbonyldiimidazole (CDI) to form an activated anhydride are provided herein. For example, processes comprising reacting Compound 9

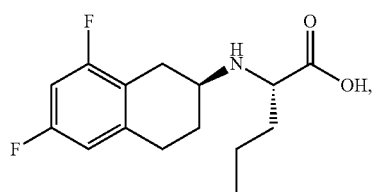

with 1,1'-carbonyldiimidazole under conditions suitable to form Compound 10

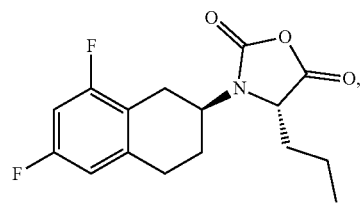

or a pharmaceutically acceptable salt thereof, are described herein. In some aspects, the process of forming Compound 10, or a pharmaceutically acceptable salt thereof, occurs in the presence of a polar aprotic solvent. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, the process of forming Compound 10, or a pharmaceutically acceptable salt thereof, occurs in the presence of one or more additives. In some aspects, the one or more additives comprise pyridine hydrobromide. In some aspects, the one or more additives comprise triethylamine. In some aspects, Compound 10, or a pharmaceutically acceptable salt thereof, is used in a subsequent process without isolation or purification.

Processes comprising reacting Compound 10 with Compound 11

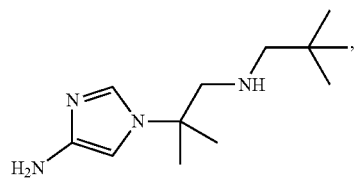

under conditions suitable to form Compound 1

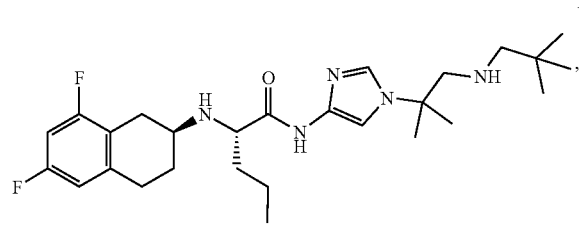

or a pharmaceutically acceptable salt thereof, are also described herein. In some aspects, the process of reacting Compound 10 with Compound 11 occurs in the presence of a polar aprotic solvent. In some aspects, the polar aprotic solvent is dimethyl sulfoxide (DMSO), N,N-dimethylformamide (DMF), acetone, tetrahydrofuran (THF), N-methyl-2-pyrrolidone (NMP), acetonitrile, or a combination thereof. In some aspects, Compound 11 is prepared without isolation or purification, and reacted with Compound 10. In some aspects, Compound 1 is neither purified nor isolated.

In some aspects, Compound 1 is the free base. In some aspects, Compound 1 is a pharmaceutically acceptable salt. In some aspects, Compound 1 is the dihydrobromide salt. In some aspects, the dihydrobromide salt of Compound 1 is a crystalline solid.

In some aspects, the process further comprises reacting Compound 1 free base with an aqueous inorganic acid under conditions suitable to form a pharmaceutically acceptable salt of Compound 1. In some aspects, the pH is adjusted to about 1 to about 1.5. In some aspects, the inorganic acid is hydrobromic acid.

In some aspects, the pharmaceutically acceptable salt of Compound 1 is isolated. In some aspects, the pharmaceutically acceptable salt of Compound 1 is the hydrobromide salt. In some aspects, the pharmaceutically acceptable salt of Compound 1 is the dihydrobromide salt.

Processes comprising reacting Compound 12

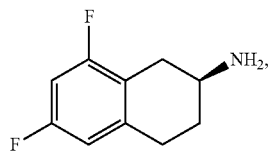

with a compound of Formula IV

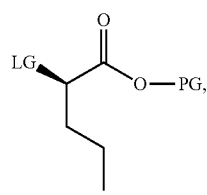

under conditions suitable to form a compound of Formula V

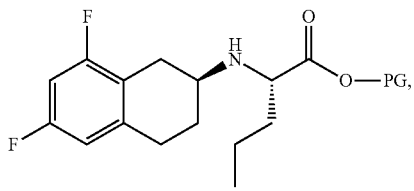

or a pharmaceutically acceptable salt thereof, are also described herein, wherein LG is a leaving group and PG is a protecting group. In some aspects, LG is —$OR^2$, $R^2$ is —$S(=O)_2R^3$, and $R^3$ is $C_1$-$C_3$ alkyl, $C_1$-$C_3$ haloalkyl, or optionally substituted phenyl. In some aspects, $R^2$ is —$S(=O)_2CF_3$. In some aspects, PG is a $C_1$-$C_6$ alkyl. In some aspects, PG is t-butyl. In some aspects, the process of forming a compound of Formula V, or a pharmaceutically acceptable salt thereof, occurs in the presence of a polar aprotic solvent. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof.

In some aspects, the process of forming a compound of Formula IV, or a pharmaceutically acceptable salt thereof, occurs in the presence of a base. In some aspects, the base is N,N-diisopropylethylamine. In some aspects, the solvent is removed in vacuo.

In some aspects, the compound of Formula V is dissolved in a polar aprotic solvent and an aqueous inorganic acid. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, a pharmaceutically acceptable salt of Formula V is isolated. In some aspects, the pharmaceutically acceptable salt of Formula V is isolated by filtration. In some aspects, the inorganic acid is hydrochloric acid. In some aspects, the pharmaceutically acceptable salt of Formula V is the hydrochloride salt.

Processes further comprising reacting a compound of Formula V, or pharmaceutically acceptable salt of thereof, with an aqueous inorganic acid in a polar protic solvent, under conditions suitable to form Compound 9

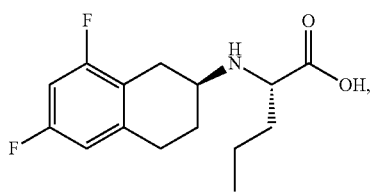

or a pharmaceutically acceptable salt thereof, are also described herein. In some aspects, in the process in which a compound of Formula V, or pharmaceutically acceptable salt thereof, is reacted with an aqueous inorganic acid, the polar protic solvent is an alcohol. In some aspects, the alcohol is isopropanol.

In some aspects, in the process in which a compound of Formula V, or pharmaceutically acceptable thereof, is reacted with an aqueous inorganic acid, the pH is adjusted to about 2.6 to about 3.0.

In some aspects, in the process in which a compound of Formula V, or pharmaceutically acceptable thereof, is reacted with an aqueous inorganic acid, Compound 9, or pharmaceutically acceptable salt thereof, is isolated. In some aspects, Compound 9, or pharmaceutically acceptable salt thereof, is isolated by filtration.

In some aspects, in the process in which a compound of Formula V, or pharmaceutically acceptable thereof, is reacted with an aqueous inorganic acid, the inorganic acid is hydrochloric acid.

The disclosure further relates to processes of preparing Compound 1, or a pharmaceutically acceptable salt thereof, by reacting Compound 10, or pharmaceutically acceptable salt thereof, with Compound 11, or pharmaceutically acceptable salt thereof. In some aspects, the process of preparing Compound 1, or a pharmaceutically acceptable salt thereof, occurs in the presence of a polar aprotic solvent. In some aspects, the polar aprotic solvent is dimethyl sulfoxide (DMSO), N,N-dimethylformamide (DMF), acetone, tetrahydrofuran (THF), N methyl-2-pyrrolidone (NMP), acetonitrile, or a combination thereof.

Processes comprising reacting Compound 1 free base, prepared by any of the processes described above, with an aqueous inorganic acid under conditions suitable to form a pharmaceutically acceptable salt of Compound 1 are provided herein. In some aspects, the pH of the process of Compound 1 free base with an aqueous inorganic acid is about 1 to about 1.5. In some aspects, the inorganic acid is hydrobromic acid. In some aspects, the pharmaceutically acceptable salt of Compound 1 is isolated. In some aspects, the pharmaceutically acceptable salt of Compound 1 is the hydrobromide salt. In some aspects, the pharmaceutically acceptable salt of Compound 1 is the dihydrobromide salt.

The disclosure further relates to processes comprising reacting Compound 9 in a solvent with 1,1'-carbonyldiimidazole under conditions suitable to form Compound 10, wherein the process further comprises reacting Compound 10 with Compound 11 under conditions suitable to form Compound 1, or a pharmaceutically acceptable salt thereof. In some aspects, the process of forming Compound 1, or a pharmaceutically acceptable salt thereof, occurs in the presence of a polar aprotic solvent. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, the process of forming Compound 1, or a pharmaceutically acceptable salt thereof, occurs in the presence of one or more additives. In some aspects, the one or more additives comprise pyridine hydrobromide. In some aspects, the one or more additives comprise triethylamine.

In some aspects, the process further comprises reacting Compound 1 free base with an aqueous inorganic acid under conditions suitable to form a pharmaceutically acceptable salt of Compound 1. In some aspects, the pH is adjusted to about 1 to about 1.5. In some aspects, the aqueous inorganic acid is hydrobromic acid.

The disclosure further relates to processes comprising reacting a pharmaceutically acceptable salt of Compound 1 with an aqueous inorganic acid in an alcohol. In some aspects, the alcohol is isopropanol. In some aspects, the pH is adjusted to about 3 to about 3.5. In some aspects, a pharmaceutically acceptable salt of Compound 1 is isolated. In some aspects, the pharmaceutically acceptable salt of Compound 1 is isolated by filtration. In some aspects, the aqueous inorganic acid is hydrobromic acid.

In some aspects, Compound 1 is synthesized by any one of the processes described above. In some aspects, the pharmaceutically acceptable salt of Compound 1 of the processes described herein is isolated. In some aspects, the pharmaceutically acceptable salt of Compound 1 is the hydrobromide salt. In some aspects, the pharmaceutically acceptable salt of Compound 1 is the dihydrobromide salt.

The disclosure further relates to compositions comprising 98.0% to 99.9% of a Compound 1, or a pharmaceutically acceptable salt thereof, and one or more of the following:

(1) 0.7% to 0.01% of a compound of Formula II:

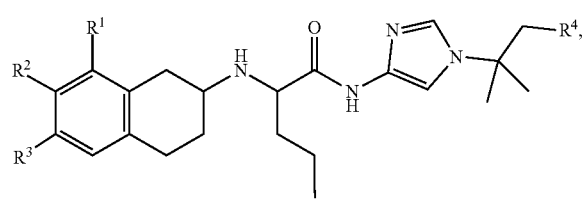

II wherein:
$R^1$ is selected from the group consisting of hydrogen, fluoro, or chloro;
$R^2$ is selected from the group consisting of hydrogen or chloro;
$R^3$ is selected from the group consisting of fluoro, or chloro; and
$R^4$ is selected from the group consisting of —OH and —N(H)CH$_2$C(CH$_3$)$_3$,
or a pharmaceutically acceptable salt thereof;

(2) 0.05% to 0.005% of imidazole, or a pharmaceutically acceptable salt thereof; or (3) 0.7% to 0.01% of a compound of Formula II, or a pharmaceutically acceptable salt thereof, and 0.05% to 0.005% of imidazole, or a pharmaceutically acceptable salt thereof, wherein the compound of Formula II is not Compound 1, and the percentages of Compound 1, the compound of Formula II, and/or imidazole are determined by high performance liquid chromatography. In some aspects, the compound of Formula II is a hydrobromide salt. In some aspects, Compound 1 is a hydrobromide salt. In some aspects, Compound 1 is a dihydrobromide salt.

In some aspects, the compound of Formula II is a compound of Formula II-A

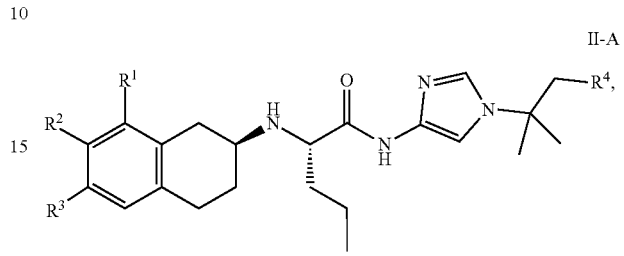

II-A or a pharmaceutically acceptable salt thereof. In some aspects, the compound of Formula II-A is a hydrobromide salt. In some aspects, the compound of Formula II-A is a dihydrobromide salt.

In some aspects, the compound of Formula II is a compound of Formula II-B

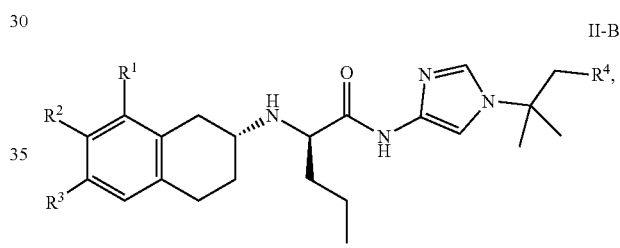

II-B or a pharmaceutically acceptable salt thereof. In some aspects, the compound of Formula II-B is a hydrobromide salt. In some aspects, the compound of Formula TI-B is a dihydrobromide salt.

In some aspects, the compound of Formula II is a compound of Formula II-C:

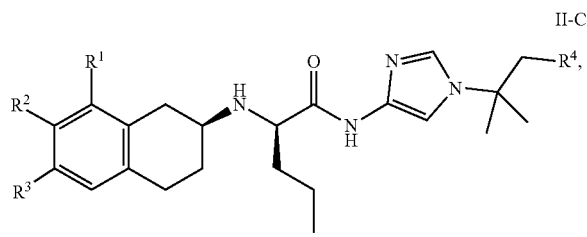

II-C or a pharmaceutically acceptable salt thereof. In some aspects, the compound of Formula II-C is a hydrobromide salt. In some aspects, the compound of Formula TI-C is a dihydrobromide salt.

In some aspects, the compound of Formula II is a compound of Formula II-D

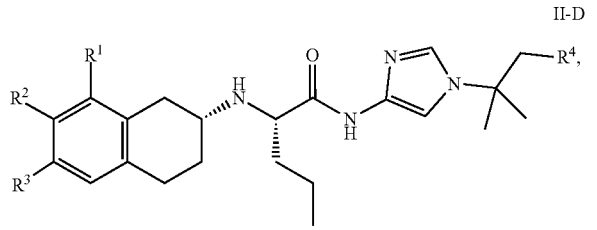
II-D or a pharmaceutically acceptable salt thereof. In some aspects, the compound of Formula II-D is a hydrobromide salt. In some aspects, the compound of Formula II-D is a dihydrobromide salt.

In some aspects, $R^4$ is —N(H)CH$_2$C(CH$_3$)$_3$. In some aspects, $R^4$ is —OH. In some aspects, $R^1$ is fluoro, $R^2$ is hydrogen, and $R^3$ is chloro. In some aspects, $R^1$ is chloro, $R^2$ is hydrogen, and $R^3$ is fluoro. In some aspects, $R^1$ is hydrogen, $R^2$ is chloro, and $R^3$ is fluoro. In some aspects, $R^1$ is fluoro, $R^2$ is hydrogen, and $R^3$ is fluoro.

The disclosure further relates to compositions comprising 98.0% to 99.9% of Compound 1, or a pharmaceutically acceptable salt thereof, and 0.6% to 0.01% of Compound 2

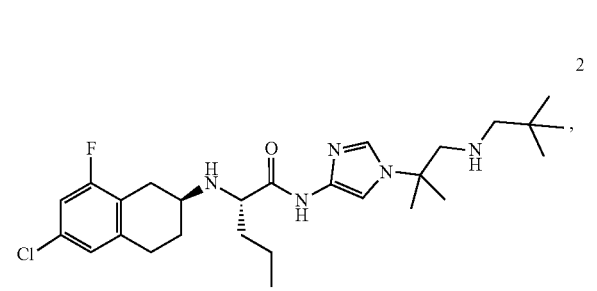 [SMILES: CCC[C@H](N[C@H]1CCc2cc(Cl)cc(F)c2C1)C(=O)Nc1cn(C(C)(C)CNCC(C)(C)C)cn1]
2 or a pharmaceutically acceptable salt thereof. In some aspects, Compound 2 is a hydrobromide salt. In some aspects, Compound 2 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.3% to 0.01% of Compound 3

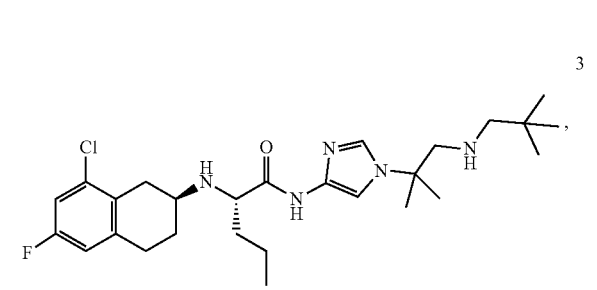 [SMILES: CCC[C@H](N[C@H]1CCc2cc(F)cc(Cl)c2C1)C(=O)Nc1cn(C(C)(C)CNCC(C)(C)C)cn1]
3 or a pharmaceutically acceptable salt thereof. In some aspects, Compound 3 is a hydrobromide salt. In some aspects, Compound 3 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 4

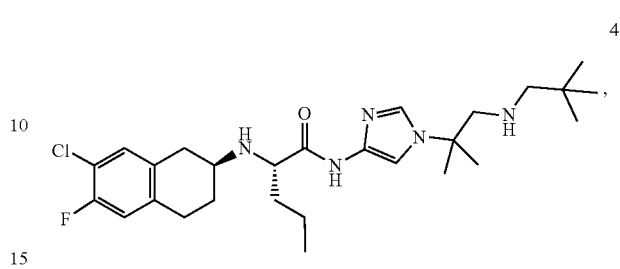
4 or a pharmaceutically acceptable salt thereof. In some aspects, Compound 4 is a hydrobromide salt. In some aspects, Compound 4 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 5

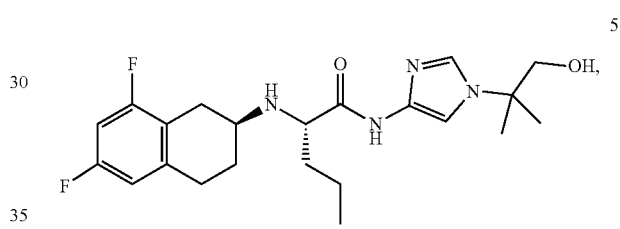
5 or a pharmaceutically acceptable salt thereof. In some aspects, Compound 5 is a hydrobromide salt. In some aspects, Compound 5 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 6

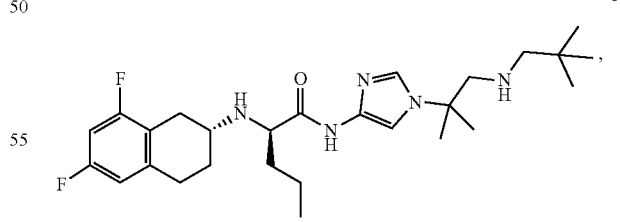
6 or a pharmaceutically acceptable salt thereof. In some aspects, Compound 6 is a hydrobromide salt. In some aspects, Compound 6 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of

7

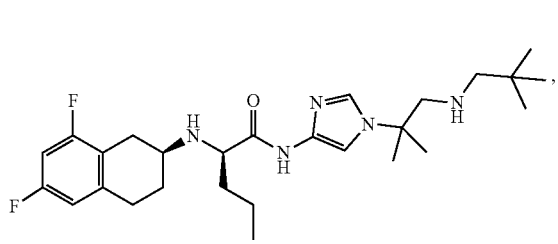

or a pharmaceutically acceptable salt thereof. In some aspects, Compound 7 is a hydrobromide salt. In some aspects, Compound 7 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 8

8

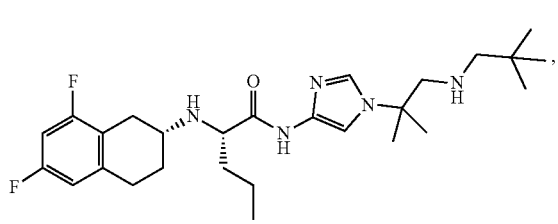

or a pharmaceutically acceptable salt thereof. In some aspects, Compound 8 is a hydrobromide salt. In some aspects, Compound 8 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.05% to 0.005% of imidazole, or a pharmaceutically acceptable salt thereof. In some aspects, the imidazole is a hydrobromide salt. In some aspects, Compound 1 is a hydrobromide salt. In some aspects, Compound 1 is a dihydrobromide salt.

The disclosure further relates to processes for preparing a composition with an active agent susceptible to oxidation that is substantially free of Compound 13

13

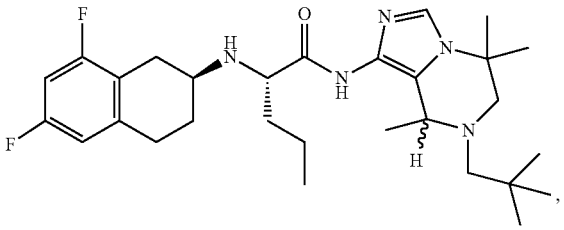

comprising the steps of dissolving Compound 11 in a solvent and combining the solution of Compound 11 with Compound 9 to form a mixture that is treated with hydrobromic acid. In some aspects, the active agent susceptible to oxidation is a hydrobromide salt of Compound 1. In some aspects, the active agent susceptible to oxidation is a dihydrobromide salt of Compound 1.

In some aspects, the solvent used to dissolve Compound 11 is an alcohol of the formula R—OH, wherein R is an alkyl, with the proviso that R is not ethyl. In some aspects, the solvent is a primary alcohol other than ethanol. In some aspects, the solvent is a secondary alcohol. In some aspects, the solvent is a tertiary alcohol. In some aspects, the solvent is 2-methylpropan-1-ol. In some aspects, the solvent is propanol. In some aspects, the solvent is isopropanol. In some aspects, the mixture is warmed to 0-5° C. during hydrobromic acid treatment.

In some aspects, the mixture is maintained at a pH less than 6. In some aspects, the mixture is maintained at a pH less than 3.

The disclosure further relates to processes for preparing a composition of Compound 1, which is essentially free of Compound 13, comprising the steps of combining Compound 10 with Compound 11 to form a mixture that is treated with hydrobromic acid in a solvent. In some aspects, the composition of Compound 1 is a hydrobromide salt. In some aspects, the composition of Compound 1 is a dihydrobromide salt.

In some aspects, Compound 1 is synthesized by any one of the processes described above.

DETAILED DESCRIPTION

Definitions and Abbreviations

As used above, and throughout the description, the following terms, unless otherwise indicated, shall be understood to have the following meanings.

Unless stated otherwise, the terms "a" and "an" and "the" and similar references used in the context of describing a particular aspect of the application (especially in the context of claims) can be construed to cover both the singular and the plural. The recitation of ranges of values herein is merely intended to serve as a shorthand process of referring individually to each separate value falling within the range. Unless otherwise indicated herein, each individual value is incorporated into the specification as if it were individually recited herein.

The term "alkyl" means any monovalent, saturated straight, branched or cyclic hydrocarbon group. Examples of "alkyl" groups include methyl, ethyl, isopropyl, and the like.

The term "haloalkyl" as used by itself or as part of another group refers to an alkyl group substituted by one or more fluorine, chlorine, bromine and/or iodine atoms.

The term "substituted" refers to independent replacement of one or more hydrogen atoms on the substituted moiety with substituents independently selected from the group of substituents as specified for a particular group. In general, a non-hydrogen substituent can be any substituent that can be bound to an atom of the given moiety that is specified to be substituted.

The term "leaving group" as used herein refers to group that departs with a pair of electrons in heterolytic bond cleavage. Common leaving groups are halides such as Cl⁻, Br⁻, and I⁻, and sulfonate esters such as tosylate (TsO⁻).

The term "protecting group" as used herein refers to group that blocks, i.e., protects, the amine functionality while reactions are carried out on other functional groups or parts of the molecule. Those skilled in the art will be familiar with the selection, attachment, and cleavage of protecting groups and will appreciate that different protective groups are known in the art, the suitability of one protective group or another being dependent on the particular the synthetic scheme planned. Treatises on the subject are available for consultation, such as Wuts, "Greene's Protective Groups in Organic Synthesis", 5th Ed., J. Wiley & Sons, Inc., NY, 2014. Suitable protecting groups include carbobenzyloxy (Cbz), tert-butyloxycarbonyl (BOC), 9-fluorenylmethyloxycarbonyl (FMOC) and benzyl (Bn) groups.

The term "base" as used herein refers to an organic proton acceptor. Non limiting bases include non-nucleophilic tertiary amines, e.g., $NEt_3$, N,N-Diisopropylethylamine, and nitrogen-containing heteroaromatic groups such as pyridine, and derivatives of pyridine, e.g., 2,4,6-trimethylpyridine.

The terms "isolate," "isolated," "isolation," and "isolating" as used herein mean a substance remains alone or apart from a solution.

The terms "purify," "purified," "purification," and "purifying" as used herein mean the removal of contaminants from a substance of interest, e.g., Compound 1.

Nirogacestat Synthesis

Processes comprising reacting a novaline moiety with 1,1'-carbonyldiimidazole (CDI) to form an activated anhydride are described herein. The process can then be followed by coupling the activated anhydride with an imidazole amine to afford Nirogacestat, or a pharmaceutically acceptable salt thereof (e.g., dihydrobromide). This coupling reaction minimizes any loss of stereochemical integrity of the norvaline moiety through buffering CDI with pyridine hydrobromide. All steps avoid aqueous workups and distillations while enabling facile crystallizations. The isolation of Nirogacestat, or pharmaceutically acceptable salt thereof (e.g., dihydrobromide) is well-designed, providing crystalline material in high yield and purity.

The disclosure also relates to processes of preparing Compound 1, or a pharmaceutically acceptable salt thereof (e.g., dihydrobromide), comprising reacting a novaline moiety directly with an imidazole amine in the presence of an alcohol other than ethanol to yield nirogacestat. This process limits the impurity in the final product of nirogacestat.

Processes comprising reacting Compound 9

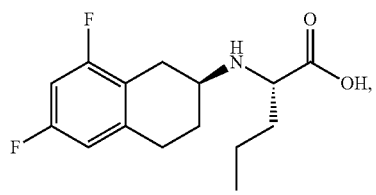

9 with 1,1'-carbonyldiimidazole under conditions suitable to form Compound 10

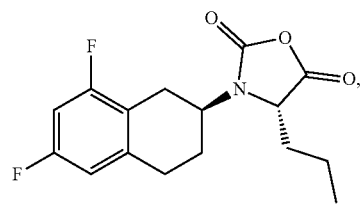

10 or a pharmaceutically acceptable salt thereof, are described herein. In some aspects, the 1,1'-carbonyldiimidazole is present in the process in an amount of about 1 to about 2 equivalents of Compound 9. In some aspects, the 1,1'-carbonyldiimidazole is present in the process in an amount of about 1.1 equivalents of Compound 9.

In some aspects, the process of forming Compound 10, or a pharmaceutically acceptable salt thereof, occurs in the presence of a polar aprotic solvent. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, the polar aprotic solvent is acetonitrile.

In some aspects, the process of forming Compound 10, or a pharmaceutically acceptable salt thereof, occurs in the presence of one or more additives. In some aspects, the one or more additives comprises pyridine hydrobromide. In some aspects, the pyridine hydrobromide is present in the process in an amount of about 2 to about 3 equivalents of Compound 9. In some aspects, the pyridine hydrobromide is present in the process in an amount of about 2.1 equivalents of Compound 9. In some aspects, the one or more additives comprises triethylamine. In some aspects, the triethylamine is present in the process in an amount of about 0.1 to 1 equivalents of Compound 9. In some aspects, the triethylamine is present in the process in an amount of about 0.7 equivalents of Compound 9.

In some aspects, the process of preparing Compound 10, or a pharmaceutically acceptable salt thereof, occurs at a temperature from about 20° C. to about 30° C. In some aspects, the process of preparing Compound 10, or a pharmaceutically acceptable salt thereof, takes about four hours.

In some aspects, the process of forming Compound 10, or a pharmaceutically acceptable salt thereof, is sampled for HPLC analysis. In some aspects, the process of forming Compound 10, or a pharmaceutically acceptable salt thereof, stops until HPLC area % of Compound 9 is less than 10.0 area %. In some aspects, the process of forming Compound 10, or a pharmaceutically acceptable salt thereof, stops until HPLC area % of Compound 9 is less than 2.0 area %. In some aspects, the difference between two consecutive Compound 9 HPLC analysis is less than 0.5 area %. In some aspects, the process of forming Compound 10, or a pharmaceutically acceptable salt thereof, is cooled to a temperature from about −15° C. to about −5° C. In some aspects, the process of forming Compound 10, or a pharmaceutically acceptable salt thereof, is cooled to a temperature of about −7° C. In some aspects, Compound 10 is used in a subsequent process without isolation or purification.

The disclosure relates to processes comprising reacting a pharmaceutically acceptable salt of Compound 11

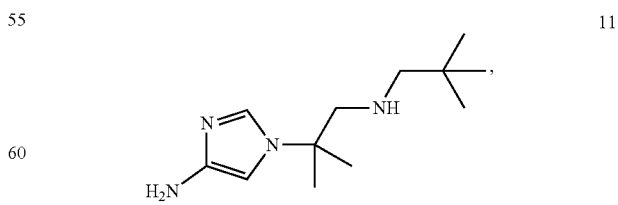

11 with a base in the presence of a polar aprotic solvent. In some aspects, the pharmaceutically acceptable salt of Compound 11 is a hydrobromide salt. In some aspects, the pharmaceutically acceptable salt of Compound 11 is a dihydrobromide salt. In some aspects, Compound 11 is a free base. In some aspects, the base is selected from the group consisting of trimethylamine, triethylamine, N,N-Diisopropylethylamine, and pyridine. In some aspects, the base is triethylamine. In some aspects, the triethylamine is present in the process in an amount of about 2 to about 5 equivalents of Compound 11. In some aspects, the triethylamine is present in the process in an amount of about 3.1 equivalents of Compound 11. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, the polar aprotic solvent is acetonitrile. In some aspects, the process of preparing Compound 11, or a free base thereof, occurs at a temperature from about −15° C. to about −5° C. In some aspects, the process of preparing Compound 11, or a free base thereof, occurs at a temperature of about −7° C. In some aspects, Compound 11 is used in a subsequent process without isolation or purification.

Processes comprising reacting Compound 10 with Compound 11 under conditions suitable to form Compound 1

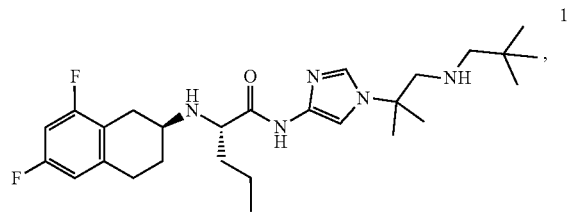 [SMILES: CCC[C@H](N[C@H]1CCc2cc(F)cc(F)c2C1)C(=O)Nc1cn(C(C)(C)CNCC(C)(C)C)cn1]

or a pharmaceutically acceptable salt thereof are also described herein. In some aspects, Compound 11 is a free base. In some aspects, Compound 11 is present in the process in an amount of about 1 to about 2 equivalents of Compound 10. In some aspects, Compound 11 is present in the process in an amount of about 1.2 equivalents of Compound 10. In some aspects, the process of reacting Compound 10 with Compound 11 occurs in the presence of a polar aprotic solvent. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, the polar aprotic solvent is acetonitrile. In some aspects, the process of reacting Compound 10 with Compound 11 occurs at a temperature from about −15° C. to about 0° C. In some aspects, the process of reacting Compound 10 with Compound 11 occurs at a temperature of about −7° C. In some aspects, the process of reacting Compound 10 with Compound 11 takes about six hours. In some aspects, the process of reacting Compound 10 with Compound 11 is sampled for HPLC analysis. In some aspects, the process of reacting Compound 10 with Compound 11 stops until HPLC area % of Compound 10 is less than 5.0 area %. In some aspects, the process of reacting Compound 10 with Compound 11 stops until HPLC area % of Compound 10 is less than 1.0 area %. In some aspects, the difference between two consecutive Compound 10 HPLC analysis is less than 0.5 area %. In some aspects, the pharmaceutically acceptable salt of Compound 1 is a hydrobromide salt. In some aspects, the pharmaceutically acceptable salt of Compound 1 is a dihydrobromide salt. In some aspects, Compound 1 is a free base. In some aspects, Compound 1 is neither purified nor isolated.

The process further comprises reacting Compound 1 free base with an aqueous inorganic acid under conditions suitable to form a pharmaceutically acceptable salt of Compound 1. In some aspects, the inorganic acid is hydrobromic acid. In some aspects, hydrobromic acid is present in the process in an amount of about 5 to about 10 equivalents of Compound 10. In some aspects, hydrobromic acid is present in the process in an amount of about 7.5 equivalents of Compound 10.

In some aspects, the process of forming a pharmaceutically acceptable salt of Compound 1 occurs at a temperature from about 30° C. to about 50° C. In some aspects, the process of forming a pharmaceutically acceptable salt of Compound 1 occurs at a temperature of about 40° C. In some aspects, the process of forming a pharmaceutically acceptable salt of Compound 1 occurs in the presence of one or more additives. In some aspects, the one or more additives comprise triethylamine. In some aspects, the pH of the process of forming a pharmaceutically acceptable salt of Compound 1 is adjusted to about 1.0 to about 1.5. In some aspects, the seeds of a pharmaceutically acceptable salt of Compound 1 is added. In some aspects, the amount of the seeds is about 0.1 wt %. In some aspects, the process of forming a pharmaceutically acceptable salt of Compound 1 is cooled at a temperature from about −15° C. to about 0° C. In some aspects, the process of forming a pharmaceutically acceptable salt of Compound 1 is cooled at a temperature of about −5° C. In some aspects, the pharmaceutically acceptable salt of Compound 1 is isolated. In some aspects, the pharmaceutically acceptable salt of Compound 1 is isolated as a crystalline solid. In some aspects, the pharmaceutically acceptable salt of Compound 1 is a hydrobromide salt. In some aspects, the pharmaceutically acceptable salt of Compound 1 is a dihydrobromide salt.

Processes comprising reacting Compound 12

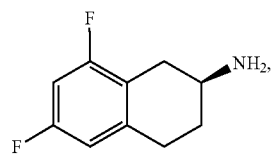

with a compound of Formula IV

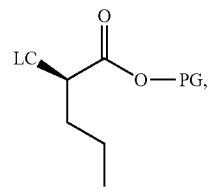

under conditions to form a compound of Formula V

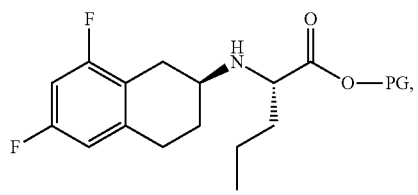

or a pharmaceutically acceptable salt thereof are also described herein, wherein LG is a leaving group; and PG is a protecting group. In some aspects, LG is —OR²; R² is —S(=O)₂R³; and R³ is $C_1$-$C_3$ alkyl, $C_1$-$C_3$ haloalkyl, or optionally substituted phenyl. In some aspects, R² is —S(=O)₂CF₃. In some aspects, PG is a $C_1$-$C_6$ alkyl. In some aspects, PG is t-butyl. In some aspects, the process of forming a compound of Formula V, or a pharmaceutically acceptable salt thereof, occurs in the presence of a polar aprotic solvent. In some aspects, the polar aprotic solvent is dichloromethane, dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, the polar aprotic solvent is dichloromethane. In some aspects, the process of forming a compound of Formula V, or a pharmaceutically acceptable salt thereof, occurs at a temperature from about 20° C. to about 30° C. In some aspects, the process of forming a compound of Formula V, or a pharmaceutically acceptable salt thereof, occurs at a temperature of about 30° C. In some aspects, the process of forming a compound of Formula V, or a pharmaceutically acceptable salt thereof, takes about ten hours. In some aspects, the process of forming a compound of Formula V, or a pharmaceutically acceptable salt thereof, is sampled for HPLC analysis. In some aspects, the process of forming a compound of Formula V, or a pharmaceutically acceptable salt thereof, stops until HPLC area % of Compound 12 is less than 2.0 area %. In some aspects, the process of forming a compound of Formula V, or a pharmaceutically acceptable salt thereof, stops until HPLC area % of Compound 12 is less than 1.0 area %. In some aspects, the difference between two consecutive Compound 12 HPLC analysis is less than 0.5 area %.

In some aspects, the process of forming a compound of Formula IV, or a pharmaceutically acceptable salt thereof, occurs in the presence of a base. In some aspects, the base is N,N-diisopropylethylamine. In some aspects, the solvent is removed in vacuo.

In some aspects, the compound of Formula V is dissolved in a polar aprotic solvent and an aqueous inorganic acid. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, the polar aprotic solvent is 1,4-dioxane. In some aspects, the inorganic acid is hydrochloric acid. In some aspects, the process of forming a compound of Formula V, or a pharmaceutically acceptable salt thereof, occurs at a temperature from about 15° C. to about 25° C. In some aspects, the process of forming a compound of Formula V, or a pharmaceutically acceptable salt thereof, takes about 1 to 2 hours. In some aspects, a pharmaceutically acceptable salt of Formula V is isolated. In some aspects, the pharmaceutically acceptable salt of Formula V is isolated by filtration. In some aspects, the pharmaceutically acceptable salt of Formula V is a hydrochloride salt.

Processes further comprising reacting a compound of Formula V, or pharmaceutically acceptable salt of thereof, with an aqueous inorganic acid in a polar protic solvent, under conditions suitable to form Compound 9

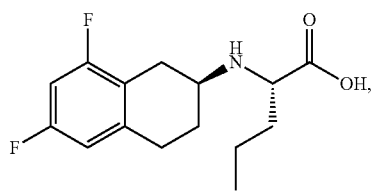

or a pharmaceutically acceptable salt thereof, are also described herein. In some aspects, in the process in which a compound of Formula V, or pharmaceutically acceptable salt thereof, is reacted with an aqueous inorganic acid, the polar protic solvent is an alcohol. In some aspects, the alcohol is isopropanol. In some aspects, in the process in which a compound of Formula V, or pharmaceutically acceptable salt thereof, is reacted with an aqueous inorganic acid, the inorganic acid is hydrochloric acid. In some aspects, the hydrochloric acid is present in the process in an amount of about 2 to about 6 equivalents of Formula V. In some aspects, the hydrochloric acid is present in the process in an amount of about 4.1 equivalents of Formula V.

In some aspects, the process of forming Compound 9 occurs at a temperature from about 50° C. to about 70° C. In some aspects, the process of forming Compound 9 occurs at a temperature from about 58° C. to about 62° C. In some aspects, the process of forming Compound 9 occurs at a temperature from about 63° C. to about 67° C. In some aspects, in the process in which a compound of Formula V, or pharmaceutically acceptable salt thereof, is reacted with an aqueous inorganic acid, the pH is adjusted to about 0.2 to about 0.6. In some aspects, in the process in which a compound of Formula V, or pharmaceutically acceptable salt thereof, is reacted with an aqueous inorganic acid, the pH is adjusted to about 1.2 to about 2.5. In some aspects, in the process in which a compound of Formula V, or pharmaceutically acceptable salt thereof, is reacted with an aqueous inorganic acid, the pH is adjusted to about 2.6 to about 3.0. In some aspects, the process of forming Compound 9 occurs in the presence of one or more additives. In some aspects, the one or more additives comprise sodium hydroxide. In some aspects, the process of forming Compound 9 is cooled at a temperature from about 15° C. to about 20° C. In some aspects, Compound 9, or pharmaceutically acceptable salt thereof, is isolated. In some aspects, Compound 9, or pharmaceutically acceptable salt thereof, is isolated by filtration.

The disclosure further relates to processes of preparing Compound 1, or a pharmaceutically acceptable salt thereof, by reacting Compound 10, or pharmaceutically acceptable salt thereof, with Compound 11, or pharmaceutically acceptable salt thereof. In some aspects, the process of preparing Compound 1, or a pharmaceutically acceptable salt thereof, occurs in the presence of a polar aprotic solvent. In some aspects, the polar aprotic solvent is dimethyl sulfoxide (DMSO), N,N-dimethylformamide (DMF), acetone, tetrahydrofuran (THF), N methyl-2-pyrrolidone (NMP), acetonitrile, or a combination thereof. In some aspects, the polar aprotic solvent is acetonitrile.

Processes comprising reacting Compound 1 free base, prepared by any of the processes described above, with an aqueous inorganic acid under conditions suitable to form a pharmaceutically acceptable salt of Compound 1 are provided herein. In some aspects, the pH of the process of Compound 1 free base with an aqueous inorganic acid is about 1 to about 1.5. In some aspects, the inorganic acid is hydrobromic acid. In some aspects, the pharmaceutically acceptable salt of Compound 1 is isolated. In some aspects, the pharmaceutically acceptable salt of Compound 1 is the hydrobromide salt. In some aspects, the pharmaceutically acceptable salt of Compound 1 is the dihydrobromide salt.

The disclosure further relates to processes comprising reacting Compound 9 in a solvent with 1,1'-carbonyldiimidazole under conditions suitable to form Compound 10, wherein the process further comprises reacting Compound 10 with Compound 11 under conditions suitable to form Compound 1, or a pharmaceutically acceptable salt thereof. In some aspects, the process of forming Compound 1, or a pharmaceutically acceptable salt thereof, occurs in the presence of a polar aprotic solvent. In some aspects, the polar aprotic solvent is dimethyl sulfoxide (DMSO), N,N-dimethylformamide (DMF), acetone, dichloromethane, tetrahydrofuran (THF), N-methyl-2-pyrrolidone (NMP), 1,4-dioxane, acetonitrile, or a combination thereof. In some aspects, the process Compound 1, or a pharmaceutically acceptable salt thereof, occurs in the presence of one or more additives. In some aspects, the one or more additives comprise pyridine hydrobromide. In some aspects, the one or more additives comprise triethylamine. In some aspects, the process further comprises reacting Compound 1 free base with an aqueous inorganic acid under conditions suitable to form a pharmaceutically acceptable salt of Compound 1. In some aspects, the pH is adjusted to about 1 to about 1.5. In some aspects, the aqueous inorganic acid is hydrobromic acid.

The disclosure further relates to processes comprising reacting a pharmaceutically acceptable salt of Compound 1 with an aqueous inorganic acid in an alcohol. In some aspects, the alcohol is isopropanol. In some aspects, the aqueous inorganic acid is hydrobromic acid. In some aspects, the hydrobromic acid is present in the process in an amount of about 1 to about 3 equivalents of a pharmaceutically acceptable salt of Compound 1. In some aspects, the hydrobromic acid is present in the process in an amount of about 2 equivalents of a pharmaceutically acceptable salt of Compound 1.

In some aspects, the process of forming a pharmaceutically acceptable salt of Compound 1 occurs in the presence of one or more additives. In some aspects, the one or more additives comprise triethylamine. In some aspects, the pH of the process of forming a pharmaceutically acceptable salt of Compound 1 is about 3 to about 3.5.

In some aspects, the process of forming a pharmaceutically acceptable salt of Compound 1 occurs at a temperature from about 40° C. to about 50° C. In some aspects, the seeds of a pharmaceutically acceptable salt of Compound 1 is added. In some aspects, the amount of the seeds is about 0.5 wt %. In some aspects, the process of forming a pharmaceutically acceptable salt of Compound 1 is cooled to about 5° C. to about 15° C. In some aspects, a pharmaceutically acceptable salt of Compound 1 is isolated. In some aspects, the pharmaceutically acceptable salt of Compound 1 is isolated as a crystalline solid. In some aspects, the pharmaceutically acceptable salt of Compound 1 is isolated by filtration.

In some aspects, Compound 1 is synthesized by any one of the processes described above. In some aspects, the pharmaceutically acceptable salt of Compound 1 of the processes described herein is isolated. In some aspects, the pharmaceutically acceptable salt of Compound 1 is the hydrobromide salt. In some aspects, the pharmaceutically acceptable salt of Compound 1 is the dihydrobromide salt.

The disclosure further relates to compositions comprising 98.0% to 99.9% of a Compound 1, or a pharmaceutically acceptable salt thereof, and one or more of the following:

(1) 0.7% to 0.01% of a compound of Formula II

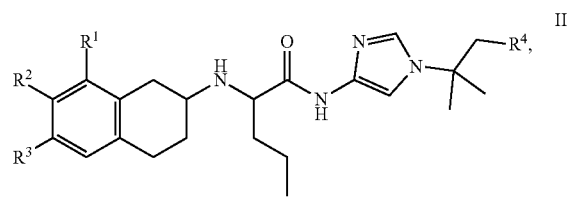

wherein:

$R^1$ is selected from the group consisting of hydrogen, fluoro, or chloro;

$R^2$ is selected from the group consisting of hydrogen or chloro;

$R^3$ is selected from the group consisting of fluoro, or chloro; and $R^4$ is selected from the group consisting of —OH and —N(H)CH$_2$C(CH$_3$)$_3$, or a pharmaceutically acceptable salt thereof;

(2) 0.05% to 0.005% of imidazole, or a pharmaceutically acceptable salt thereof; or (3) 0.7% to 0.01% of a compound of Formula II, or a pharmaceutically acceptable salt thereof, and 0.05% to 0.005% of imidazole, or a pharmaceutically acceptable salt thereof, wherein the compound of Formula II is not Compound 1, and the percentages of Compound 1, the compound of Formula II, and/or imidazole are determined by high performance liquid chromatography. In some aspects, the compound of Formula II is a hydrobromide salt. In some aspects, Compound 1 is a hydrobromide salt. In some aspects, Compound 1 is a dihydrobromide salt.

In some aspects the compound of Formula II is a compound of Formula II-A

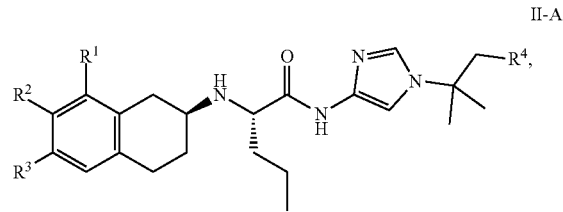

or a pharmaceutically acceptable salt thereof. In some aspects, the compound of Formula II-A is a hydrobromide salt. In some aspects, the compound of Formula II-A is a dihydrobromide salt.

In some aspects, the compound of Formula II is a compound of Formula II-B

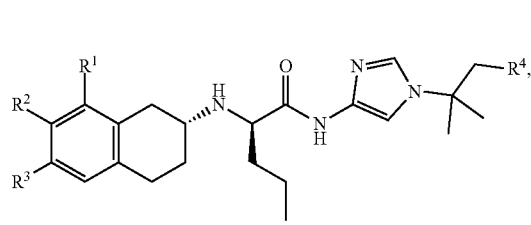
II-B or a pharmaceutically acceptable salt thereof. In some aspects, the compound of Formula II-B is a hydrobromide salt. In some aspects, the compound of Formula II-B is a dihydrobromide salt.

In some aspects, the compound of Formula II is a compound of Formula II-C

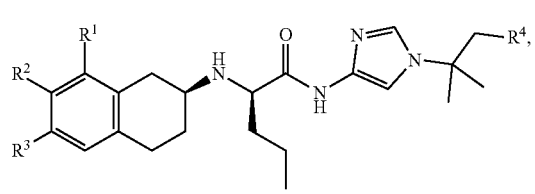
II-C or a pharmaceutically acceptable salt thereof. In some aspects, the compound of Formula II-C is a hydrobromide salt. In some aspects, the compound of Formula TI-C is a dihydrobromide salt.

In some aspects, the compound of Formula II is a compound of Formula II-D

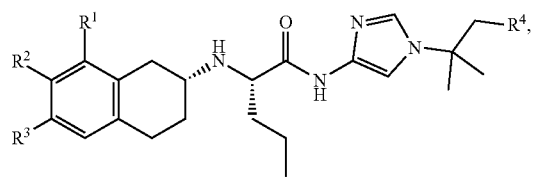
II-D or a pharmaceutically acceptable salt thereof. In some aspects, the compound of Formula II-D is a hydrobromide salt. In some aspects, the compound of Formula II-D is a dihydrobromide salt.

In some aspects, $R^4$ is —N(H)CH$_2$C(CH$_3$)$_3$. In some aspects, $R^4$ is —OH. In some aspects, $R^1$ is fluoro, $R^2$ is hydrogen, and $R^3$ is chloro. In some aspects, $R^1$ is chloro, $R^2$ is hydrogen, and $R^3$ is fluoro. In some aspects, $R^1$ is hydrogen, $R^2$ is chloro, and $R^3$ is fluoro. In some aspects, $R^1$ is fluoro, $R^2$ is hydrogen, and $R^3$ is fluoro.

The disclosure further relates to compositions comprising 98.0% to 99.9% of Compound 1, or a pharmaceutically acceptable salt thereof, and 0.6% to 0.01% of Compound 2

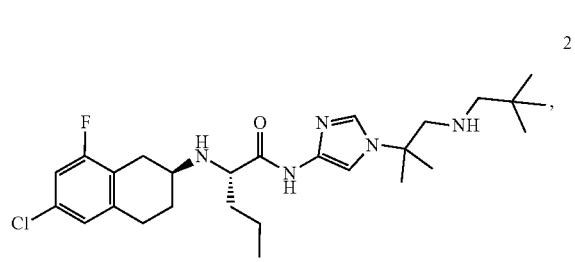 [SMILES: CCC[C@H](N[C@H]1CCc2cc(Cl)cc(F)c2C1)C(=O)Nc1cn(C(C)(C)CNCC(C)(C)C)cn1]
2 or a pharmaceutically acceptable salt thereof. In some aspects, Compound 2 is a hydrobromide salt. In some aspects, Compound 2 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.3% to 0.01% of Compound 3

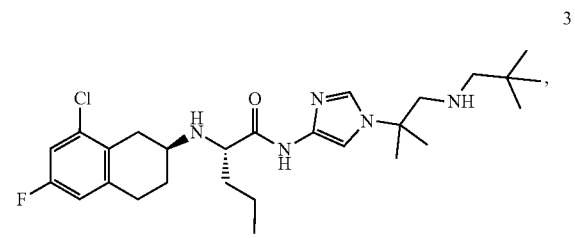 [SMILES: CCC[C@H](N[C@H]1CCc2cc(F)cc(Cl)c2C1)C(=O)Nc1cn(C(C)(C)CNCC(C)(C)C)cn1]
3 or a pharmaceutically acceptable salt thereof. In some aspects, Compound 3 is a hydrobromide salt. In some aspects, Compound 3 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 4

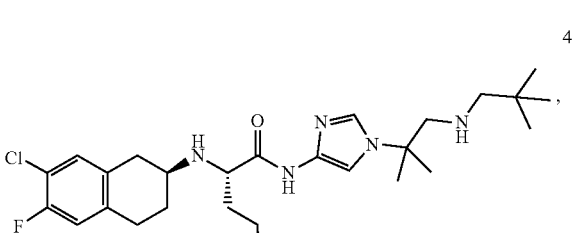
4 or a pharmaceutically acceptable salt thereof. In some aspects, Compound 4 is a hydrobromide salt. In some aspects, Compound 4 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 5

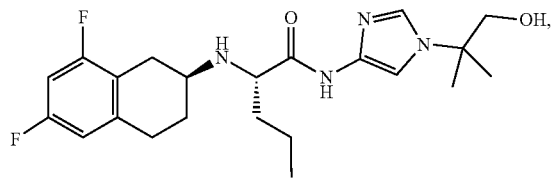

or a pharmaceutically acceptable salt thereof. In some aspects, Compound 5 is a hydrobromide salt. In some aspects, Compound 5 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 6

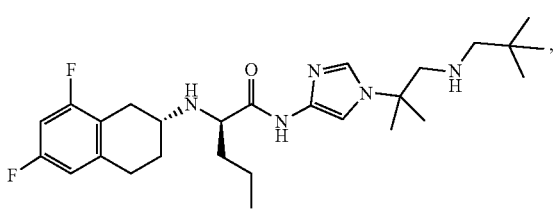

or a pharmaceutically acceptable salt thereof. In some aspects, Compound 6 is a hydrobromide salt. In some aspects, Compound 6 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 7

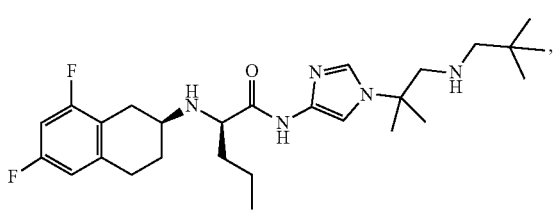

or a pharmaceutically acceptable salt thereof. In some aspects, Compound 7 is a hydrobromide salt. In some aspects, Compound 7 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.5% to 0.01% of Compound 8

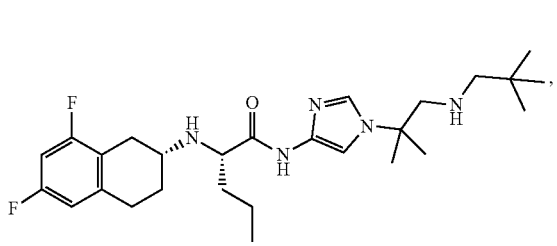

or a pharmaceutically acceptable salt thereof. In some aspects, Compound 8 is a hydrobromide salt. In some aspects, Compound 8 is a dihydrobromide salt. In some aspects, Compound 1 is a hydrobromide salt. In some aspects, Compound 1 is a dihydrobromide salt.

The disclosure further relates to compositions comprising 98.0% to 99.9% of Compound 1, or a pharmaceutically acceptable salt thereof, and 0.05% to 0.005% of imidazole, or a pharmaceutically acceptable salt thereof. In some aspects, the imidazole is a hydrobromide salt. In some aspects, Compound 1 is a hydrobromide salt. In some aspects, Compound 1 is a dihydrobromide salt.

The disclosure further relates to processes for preparing a composition with an active agent susceptible to oxidation that is substantially free of Compound 13

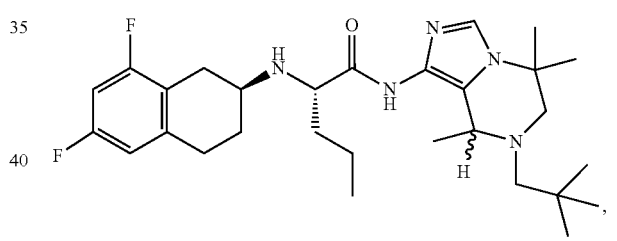

comprising the steps of dissolving Compound 11 in a solvent and combining the solution of Compound 11 with Compound 9 to form a mixture that is treated with hydrobromic acid. In some aspects, the active agent susceptible to oxidation is a hydrobromide salt of Compound 1. In some aspects, the active agent susceptible to oxidation is a dihydrobromide salt of Compound 1.

In some aspects, the solvent used to dissolve Compound 11 is an alcohol of the formula R—OH, wherein R is an alkyl, with the proviso that R is not ethyl. In some aspects, the solvent is a primary alcohol, other than ethanol. In some aspects, the solvent is a secondary alcohol. In some aspects, the solvent is a tertiary alcohol. In some aspects, the solvent is 2-methylpropan-1-ol. In some aspects, the solvent is propanol. In some aspects, the solvent is isopropanol. In some aspects, the mixture is warmed to 0-5° C. during hydrobromic acid treatment.

In some aspects, the mixture is maintained at a pH less than 6. In some aspects, the mixture is maintained at a pH less than 3.

The disclosure further relates to processes for preparing a composition of Compound 1, which is essentially free of Compound 13, comprising the steps of combining Compound 10 with Compound 11 to form a mixture that is treated with hydrobromic acid in a solvent. In some aspects, the active agent susceptible to oxidation is a hydrobromide salt of Compound 1. In some aspects, the active agent susceptible to oxidation is a dihydrobromide salt of Compound 1.

In some aspects, Compound 1 is synthesized by the any one of the processes described above.

EXAMPLES

The following synthetic examples are illustrative, but not limiting, of the methods described herein. Other suitable modifications and adaptations of the variety of conditions and parameters normally encountered in the field, and which are obvious to those skilled in the art, are within the spirit and scope of the invention.

Synthetic Example 1

Formula V with protecting group tert-butyl (1.0 equivalent) is added to isopropanol and water and reacted with aqueous hydrochloric acid (~4.1 equivalents) at approximately 58-62° C. to afford Compound 9. The solution pH is adjusted (~0.2-0.6) with sodium hydroxide, heated to approximately 65° C., and pH adjusted again to approximately 1.2-2.5. The solution is cooled (~15-20° C.) and adjusted to a final pH of approximately 2.6-3.0 to crystallize the product. Compound 9 is filtered, washed with water and isopropanol, and dried (<75° C.).

Synthetic Example 2

Compound 9 is added to acetonitrile and pyridine hydrobromide (~2.1 equivalents). 1,1'-carbonyldiimidazole (~1.1 equivalents) is added and the mixture is heated (~20-30° C.) to afford Compound 10. Triethylamine (~0.7 equivalents) and acetonitrile are added, and the mixture is cooled (~-7° C.) and carried forward into next step.

Synthetic Example 3

A dihydrobromide salt of Compound 11 (~1 equivalent) is added to acetonitrile and converted to free base Compound 11 with the addition of triethylamine (~3.1 equivalents) at approximately -7° C. This solution is carried forward into next step. SYNTHETIC EXAMPLE 4

The solution of Compound 11 (~1.20 equivalents) is combined with the solution of Compound 10 (~1 equivalent) at approximately -7° C. to afford a dihydrobromide salt of Compound 1. The reaction mixture is treated with aqueous hydrobromic acid (~7.5 equivalents) and heated to approximately 40° C. Triethylamine is added to obtain a final mixture pH of about 1 to about 1.5. The seeds of a dihydrobromide salt of Compound 1 (~0.1 wt %) are added, and the mixture is cooled (~5° C.) to crystallize the product. The crude solids of a dihydrobromide salt of Compound 1 are filtered, washed with water and acetonitrile, and dried (~40-50° C.).

Synthetic Example 5

The crude compound of a dihydrobromide salt of Compound 1 (~1 equivalent) is dissolved in isopropanol and water with aqueous hydrobromic acid (~2 equivalents). This solution is heated (about 40 to about 50° C.), neutralized with triethylamine (~1 equivalent), and the seeds of a dihydrobromide salt of Compound 1 (~0.5 wt %) are added. Triethylamine diluted in isopropanol is added in portions until the target pH (~3-3.5) is reached. The solution is cooled (~5-15° C.) to crystallize the product. The nirogacestat hydrobromide (e.g., nirogacestat dihydrobromide) solids are filtered, washed with pre-cooled (~8-12° C.) isopropanol, and dried (<65° C.).

Synthetic Example 6

A dry and clean reactor was evacuated and then filled with nitrogen. Methyl tert-butyl ether (MTBE) and purified water were charged into the reactor at about 15 to about 25° C. The mixture was bubbled nitrogen under the surface to degas. At 15-25° C., hydrogen phosphate salt of Compound 12 (~1 equivalent) was added into the mixture through a solid addition funnel, and stirred for about 0.5 to about 1 hr. At about 15 to about 25° C., a sodium hydroxide solution (~2 equivalents) was added into the mixture. The mixture was sampled for pH until pH was >11. The mixture was filtered. The filter cake was rinsed with MTBE. The filtrate was settled for about 0.5 to about 2 hrs, then separated into an organic phase and an aqueous phase. The aqueous phase was washed with MTBE twice, each time stirred for about 0.5 to about 1 hr and settled for about 0.5 to about 2 hrs, then separated into an organic phase and an aqueous phase. The organic phase was collected and washed with purified water at about 15 to about 25° C. Then the organic phase was concentrated at a temperature ≤40° C. under reduced pressure until about 30 to about 45 L was left. The mixture was sampled for Karl Fischer (KF) analysis (KF≤0.1%). The free base of Compound 12 was synthesized.

Dichloromethane (DCM) was added into the reactor at about 15 to about 25° C. The mixture was stirred for about 20 to about 30 min.

DCM was added into a second reactor at about 15 to about 25° C., the mixture was sampled for KF analysis (KF≤0.1%). N,N-Diisopropylethylamine (about 3.4 equivalents) and tert-butyl (R)-2-hydroxypentanoate (about 1.7 equivalents) were added into the second reactor at about 15 to about 25° C., and then the mixture was stirred for about 10 to about 20 min. The mixture was cooled to about -20 to about -30° C.

DCM was added into a third reactor at about 15 to about 25° C., the mixture was sampled for KF analysis (KF≤0.1%). Trifluoromethansulfonic anhydride (about 2 equivalents) was added into the third reactor at about 15 to about 25° C. by pump, and then the mixture was stirred for about 10 to about 20 min. Then, the prepared DCM solution with trifluoromethansulfonic anhydride (trifluoromethansulfonic anhydride:DCM=1:6.4 equivalents) was added into the second reactor at -20~-30° C. under stirring. The mixture was allowed to react at about -20 to about -30° C. After about 0.5 to about 1 hr, the mixture was sampled every about 1 to about 2 hrs for HPLC analysis, until area % of tert-butyl (R)-2-hydroxypentanoate was 3.0 area %. A compound of Formula IV was synthesized, with a leaving group as trifluoromethanesulfonate and a protecting group as tert-butyl.

The solution of the free base of Compound 12 was added into the solution of the compound of Formula IV at a rate of about 100 to about 150 Kg/h at about -20 to about -30° C. The mixture was heated to about 20 to about 30° C. After about 10 hrs, the mixture was sampled about every 4 to 6 hrs for HPLC analysis until the area % of the free base of Compound 12 was 2.0 area % or the difference between two consecutive samples was 0.5%. Potassium bicarbonate solution (about 5.0 equivalents) was added into the mixture at about 20 to about 30° C. and the mixture was stirred for about 0.5 to about 1 hr. The mixture was transferred into a stainless steel reactor. The mixture was stirred for about 0.5 to about 1 hr at about 20 to about 30° C., settled for about 0.5 to about 1 hr, then separated into an organic phase and an aqueous phase. The organic phase was concentrated at a temperature ≤40° C. under reduced pressure until about 60 to about 90 L was left. 1,4-dioxane (about 10.0 equivalents) was added into the organic phase at a temperature ≤40° C. The mixture was concentrated at a temperature ≤40° C. under reduced pressure until about 60 to about 90 L was left. The mixture was sampled for DCM residual analysis until DCM residual was <1%. Additional 1,4-dioxane (about 10.0 equivalents) was added into the mixture at about 15 to about 25° C. and stirred for about 0.5 to about 1 hr. The mixture was then filtered. The filter cake was rinsed with 1,4-dioxane. The filtrate was transferred into a reactor at about 15 to about 25° C. and then the mixture was stirred for about 10 to about 20 min. Purified water (about 6.0 equivalents) was added to the mixture at about 15 to about 25° C. The mixture was adjusted until KF was about 1 to about 2% and then stirred for about 10 to about 20 min. 4M HCl/dioxane solution (about 2 equivalents of HCl) was added to the mixture at about 15 to about 25° C. The mixture was stirred at about 15 to about 25° C. for crystallization. After about 1 to about 2 hrs, the mixture was sampled for HPLC analysis until the mother liquid of the compound of Formula V with a tert-butyl protecting group was <0.8 wt % or the difference between two consecutive samples was <0.3%. The slurry in the mixture was filtered. The filter cake was rinsed with 1,4-dioxane three times and then the filter cake was rinsed twice with n-heptane. The solid was dried at a temperature about 40-50° C. 10 hrs later, the solid was sampled every 3~6 hrs until 1,4-dioxane residual is <0.5% and n-heptane residual is <0.5%. After drying, the solid was cooled to 15-25° C. The hydrochloride salt of a compound of Formula V was synthesized, with a protecting group as tert-butyl.

Synthetic Example 7

To obtain Compound 1, Compound 9 may be added to acetonitrile and pyridine hydrobromide (~2.1 equivalents). 1,1'-carbonyldiimidazole (~1.07 equivalents) may then be added and the mixture heated (~20-30° C.) to afford Compound 10. Triethylamine (~0.66 equivalents) and acetonitrile is then added, and the mixture cooled (~7° C.). The mixture is then combined with a solution of Compound 11 (1.20 equivalents) at approximately −7° C. to afford Compound 1. The reaction mixture is then treated with aqueous hydrobromic acid (~7.5 equivalents) and heated to approximately 40° C. Triethylamine may be added to obtain a final mixture pH of approximately 1-1.5. Compound 1 (~0.1 wt %) seeds can be added, and the mixture cooled (~5° C.) to crystallize the product. The crude solid Compound 1 is then filtered, washed with water and acetonitrile, and dried (~40-50° C.). The crude Compound 1 (1.0 equivalent) may then be dissolved in isopropanol and water with aqueous hydrobromic acid (2.0 equivalents). This solution can be heated (~40-50° C.), neutralized with triethylamine (1.0 equivalent), and seeds of Compound 1 (~0.5 wt %) again added. Triethylamine diluted in isopropanol is then added in portions until the target pH (~3-3.5) is reached. The solution is cooled (~5-15° C.) to crystallize the product. Compound 1 is then filtered, washed with pre-cooled (~8-12° C.) isopropanol, and dried (<65° C.).

What is claimed is:

1. A composition comprising 98.0% to 99.9% by weight of Compound 1 or a salt thereof prepared by a process comprising the steps of combining Compound 10

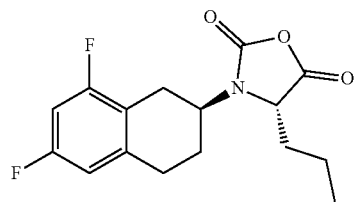

with Compound 11

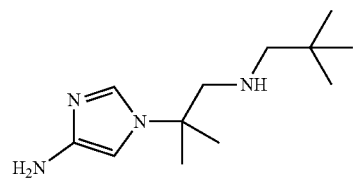

to form Compound 1, and optionally treating Compound 1 with an acid in a solvent to form a salt of Compound 1

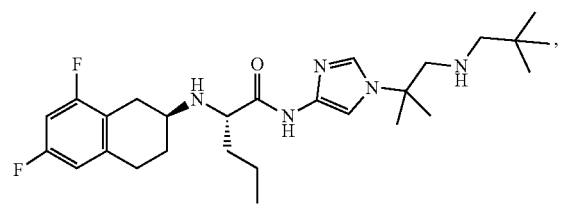

wherein the composition comprises at least one of:
(a) 0.7% to 0.01% by weight of Compound 2 having the formula

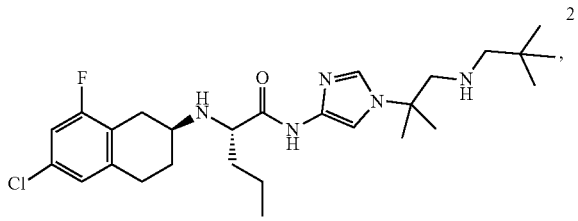 [SMILES: CCC[C@H](N[C@H]1CCc2cc(Cl)cc(F)c2C1)C(=O)Nc1cn(C(C)(C)CNCC(C)(C)C)cn1]

or a pharmaceutically acceptable salt thereof, (b) 0.7% to 0.01% by weight of Compound 3 having the formula

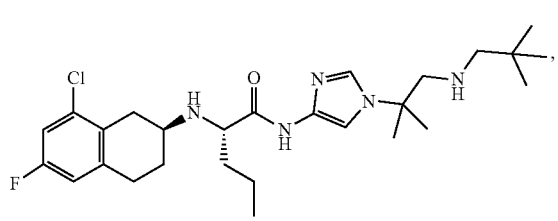

or a pharmaceutically acceptable salt thereof, or
(c) 0.7% to 0.01% by weight of Compound 4 having the formula

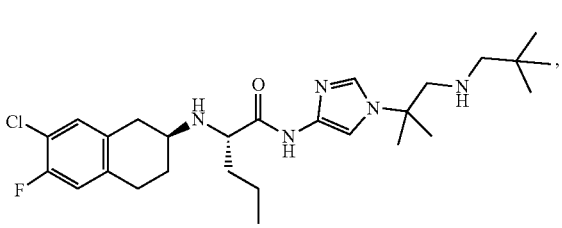

or a pharmaceutically acceptable salt thereof.

2. The composition of claim 1, wherein the composition comprises 0.7% to 0.01% by weight of Compound 2

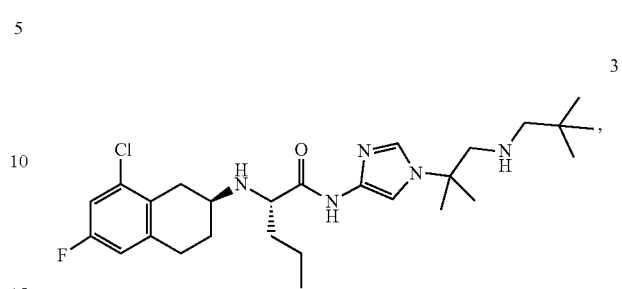

or a pharmaceutically acceptable salt thereof.

3. The composition of claim 1, wherein the composition comprises 0.7% to 0.01% by weight of Compound 3 having the formula or a pharmaceutically acceptable salt thereof.

4. The composition of claim 1, wherein the composition comprises 0.7% to 0.01% by weight of Compound 4 having the formula

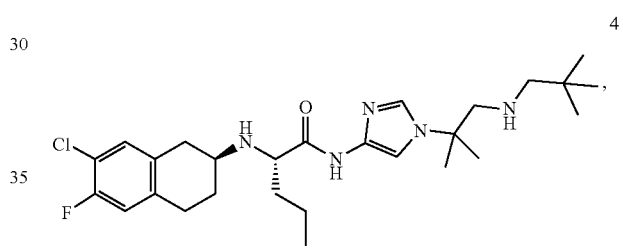

or a pharmaceutically acceptable salt thereof.

* * * * *